United States Patent [19]

Soboczenski

[11] 4,297,370

[45] Oct. 27, 1981

[54] INSECTICIDAL COMPOSITIONS

[75] Inventor: Edward J. Soboczenski, Chadds Ford, Pa.

[73] Assignee: E. I. Du Pont de Nemours and Company, Wilmington, Del.

[21] Appl. No.: 119,295

[22] Filed: Feb. 6, 1980

Related U.S. Application Data

[63] Continuation of Ser. No. 963,949, Nov. 27, 1979, abandoned, which is a continuation-in-part of Ser. No. 804,358, Jun. 7, 1977, abandoned.

[51] Int. Cl.$^3$ .................... A01N 37/00; A01N 37/08; A01N 37/34
[52] U.S. Cl. .................... 424/298; 424/304; 424/305; 424/327
[58] Field of Search ................ 424/298, 327, 304, 305

[56] References Cited

U.S. PATENT DOCUMENTS 4,004,031 1/1977 Drabek ................................ 424/300

FOREIGN PATENT DOCUMENTS 7307130 11/1973 Netherlands .
1439615 6/1976 United Kingdom .

OTHER PUBLICATIONS

All et al., J. Econ. Ent., vol. 70, No. 6 (1977), pp. 813-817.

Primary Examiner—Allen J. Robinson

[57] ABSTRACT

Control of insects using (1) cyano-(3-phenoxyphenyl)-methyl 4-chloro-α-(1-methylethyl)benzeneacetate or (3-phenoxybenzyl)cis-trans-3-(2,2-dichlorovinyl)-2,2-dimethylcyclopropanecarboxylate, and (2) a compound such as N,N'-[thiobis(methylamino)carbonyloxy]-bis[ethanimidothioic acid], dimethyl ester.

8 Claims, 4 Drawing Figures

PREDICTED VS OBSERVED FOR N,N'-[THIOBIS(METHYLAMINOCARBONYLOXY)]-BIS-[ETHANIMIDOTHIOIC ACID], DIMETHYL ESTER AND CYANO-(3-PHENOXYPHENYL)METHYL-4-CHLORO-α-(1-METHYLETHYL)-BENZENE ACETATE

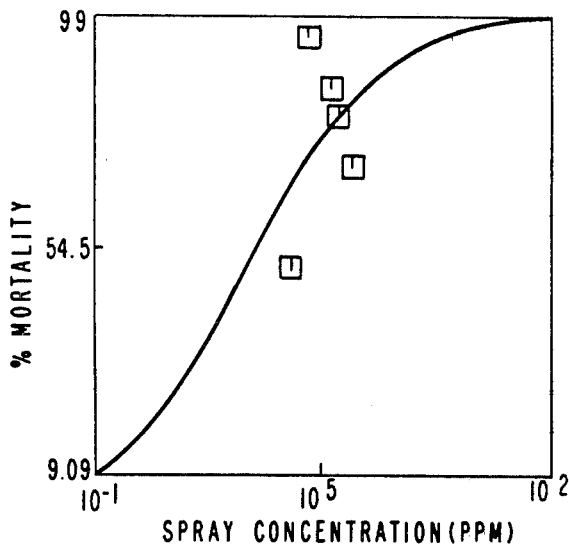

FIG. 1
(TEST I)

PREDICTED VS OBSERVED N,N-[THIOBIS(METHYLAMINOCARBONYLOXY)]-BIS-[ETHANIMIDOTHIOIC ACIDS], DIMETHYL ESTER AND (3-PHENOXYBENZYL)-CIS-TRANS-3-(2,2-DICHLOROVINYL)-2,2-DIMETHYLCYCLOPROPANE CARBOXYLATE.

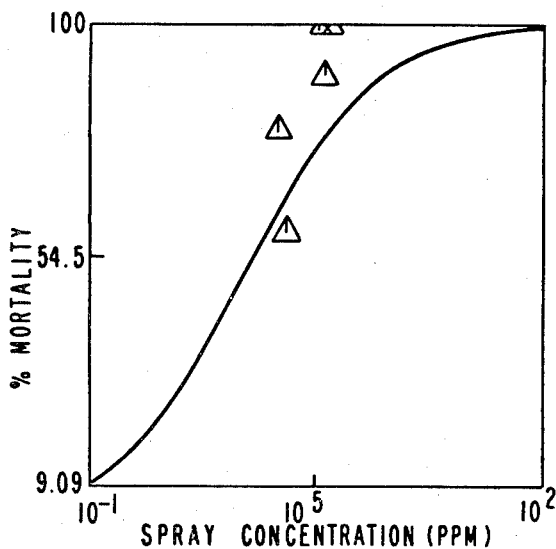

FIG. 2
(TEST I)

PREDICTED VS OBSERVED FOR N,N'-[THIOBIS(METHYLAMINOCARBONYLOXY)]-BIS-[ETHANIMIDOTHIOIC ACIDS], DIMETHYL ESTER, AND (3-PHENOXYBENZYL)-CIS-TRANS-3-(2,2-DICHLOROVINYL)-2,2-DIMETHYLCYCLOPROPANE CARBOXYLATE.

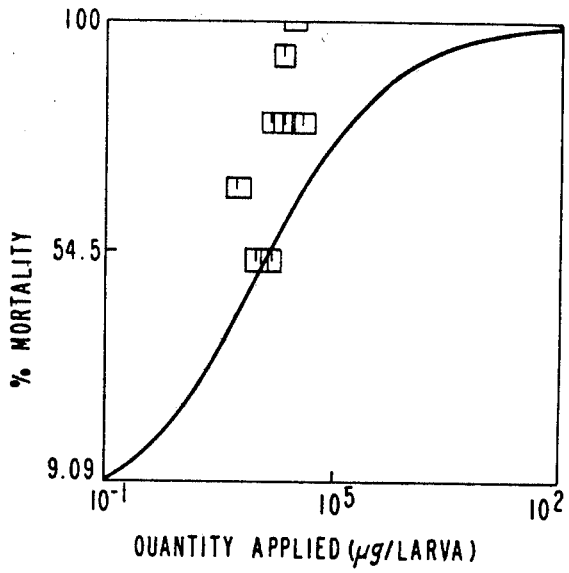

FIG. 3
(TEST 2)

PREDICTED VS OBSERVED FOR N,N'-[THIOBIS(METHYLAMINOCARBONYLOXY]-BIS-[ETHANIMIDOTHIOIC ACID], DIMETHYL ESTER AND CYANO-(3-PHENOXYPHENYL)METHYL-4-CHLORO-$\alpha$-(1-METHYLETHYL)-BENZENE ACETATE

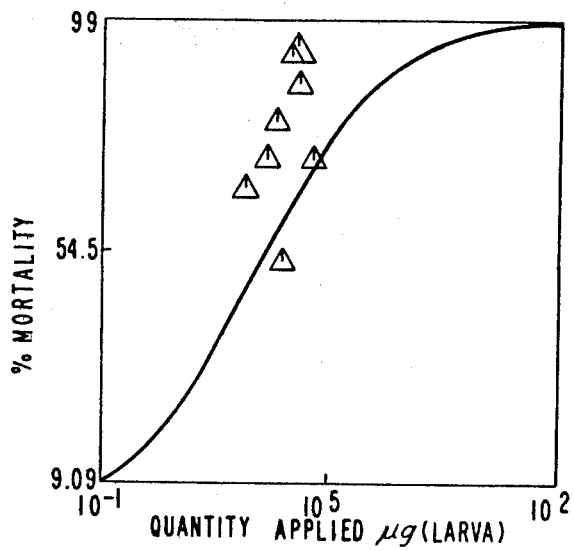

FIG. 4
(TEST 2)

INSECTICIDAL COMPOSITIONS

CROSS REFERENCE TO RELATED APPLICATIONS

This is a continuation of Application Ser. No. 963,949, filed Nov. 27, 1979 and now abandoned, which was a continuation in part of copending Application Ser. No. 804,358, filed June 7, 1977 and now abandoned.

BACKGROUND OF THE INVENTION

This invention relates to agricultural compositions containing more than one active ingredient for control of insects.

U.S. Pat. No. 3,639,633 discloses insecticidal activity of substituted O-carbamylhydroxamates which can be used alone or in combination with other named biologically active compounds. This class of O-carbamylhydroxamates includes methomyl, i.e., methyl N-[[(methylamino)carbonyl]oxy]ethanimidothioate.

U.S. Pat. No. 3,835,176 discloses combinations of insecticidal compounds including pyrethins and a compound such as methomyl.

U.S. Pat. No. 4,004,031 discloses compounds for use in pest control of the formula:

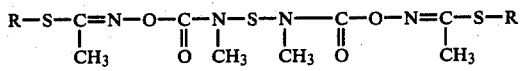

wherein R represents a $C_1$-$C_5$ alkyl radical. Other insecticides can be used in combination.

Belgian Patent No. 848,912 discloses insecticidal compounds of the formula

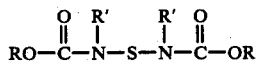

where R and R' have various substituent definitions.

Insecticidal uses of cyano-(3-phenoxyphenyl)methyl 4-chloro-α-(1-methylethyl)benzeneacetate and (3-phenoxybenzyl)cis-trans-3-(2,2-dichlorovinyl)-2,2-dimethylcyclopropanecarboxylate are disclosed respectively in U.K. Patent No. 1,439,616 and Dutch Patent No. 7,037,130.

SUMMARY OF THE INVENTION

According to this invention, there is provided agricultural compositions containing a compound of formula I and either cyano-(3-phenoxyphenyl)methyl 4-chloro-α-(1-methylethyl)benzeneacetate or (3-phenoxybenzyl) cis-trans-3-(2,2-dichlorovinyl)-2,2-dimethylcyclopropane carboxylate.

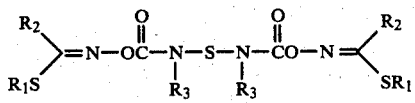

where
$R_1$ is branched or straight chain alkyl of 1—3 carbon atoms;
$R_2$ is methyl or ethyl; and
$R_3$ is hydrogen or methyl.

ILLUSTRATIVE COMPOSITIONS

Illustrative compounds of formula I suitable in the agricultural compositions of this invention are those where
(1) $R_1$ is methyl; or
(2) $R_2$ is methyl; or
(3) $R_3$ is methyl.

A preferred class of compounds of formula I is where $R_1$, $R_2$ and $R_3$ are methyl, i.e., N,N'-[thiobis(methylamino)carbonyloxy]bis-[ethanimidothioic acid], dimethyl ester.

Specifically illustrative of the combinations of this invention are:

(1) N,N'-[thiobis(methylaminocarbonyloxy)]bis-[ethanimidothioic acid], dimethyl ester and cyano-(3-phenoxyphenyl)methyl 4-chloro-α-(1-methylethyl)-benzeneacetate;

(2) N,N'-[thiobis(methylaminocarbonyloxy)]bis-[ethanimidothioic acid], dimethyl ester and (3-phenoxybenzyl)cis-trans-3-(2,2-dichlorovinyl)-2,2-dimethylcyclopropanecarboxylate.

FIGURES

FIGS. 1, 2, 3 and 4 are plotted test results of actual and predicted insecticidal activity of combinations of compounds of the present invention compared to individual cmmpounds.

DETAILED DESCRIPTION OF THE INVENTION

Insects are controlled by applying to a locus to be protected a mixture of a compound of formula I and either cyano-(3-phenoxyphenyl)methyl 4-chloro-α-(1-methylethyl)benzeneacetate, or (3-phenoxybenzyl) cis-trans-3-(2,2-dichlorovinyl)-2,2-dimethylcyclopropanecarboxylate. The exact quantities and ratios for compounds required for such insect control depend on many factors including the type and intensity of insect infestation to be controlled, the volume of foliage per unit area which needs to be protected, the time of year, the temperature, the intensity of sunlight, the amount of rainfall, the percent control desired, the method of application used, the type of crop to be protected, the interval between sprays, the length of time that control is desired, and other factors.

Ratios of combinations of formula I to either cyano-(3-phenoxyphenyl)-methyl 4-chloro-α-(1-methylethyl)-benzeneacetate, or (3-phenoxybenzyl)cis-trans-3-(2,2-dichlorovinyl)-2,2-dimethylcyclopropanecarboxylate which are suitable for direct application in insect control range from 50:1 to 1:1 by weight. Preferred are ratios of from 20:1 to 3:1, and most preferred are those from 10:1 to 5:1.

For low-volume usage such as through aerial applications to cotton, sugar beets and lettuce, spray concentrations should be in the range of from 2000–250,000 ppm of total active ingredients. As the volume of spray per acre is increased from low to moderate or high volume, the concentration of active ingredients can be correspondingly reduced.

Low infestations of easy-to-kill insects may require as little as 0.05 kg/ha of total active ingredients early in the season while high infestations of hardy species may require about 10 kg/ha to regain control latter in the season.

Compounds of formula I are disclosed in U.S. Pat. No. 4,004,031 and BE Pat. No. 848,912 and can be prepared by following the general teachings of these disclosures.

It is understood that (3-phenoxybenzyl)cis-trans-3-(2,2-dichlorovinyl)-2,2-dimethylcyclopropanecarboxylate includes optical isomers, i.e., (3-phenoxybenzyl)[=,-]-cis-trans-3-(2,2-dichlorovinyl)-2,2-dimethylcyclopropanecarboxylate. Only one of these isomers needs be present, since all are insecticidally active compounds.

In the following examples, all parts are by weight and temperatures are in degrees centigrade unless otherwise indicated.

TEST 1

The insecticidal activity toward southern armyworm larvae was determined for the compounds and mixtures shown in Table I. Red kidney beans were sprayed with individual compounds and mixtures. Two leaves of the kidney beans were confined in separate Petri dishes with 10 armyworm larvae. Two separate tests were conducted. Mortality results at the end of 72 hours were recorded.

TABLE 1

| COMPOUND | Concentration (PPM) | Percent Mortality (72 Hrs.) Test A | Percent Mortality (72 Hrs.) Test B | Average |
|---|---|---|---|---|
| N,N'-[thiobis(methyl-amino)carbonyloxy]bis-[ethanimidothioic acid], dimethyl ester | 16 | — | 100 | 100 |
|  | 8 | 100 | 90 | 95 |
|  | 4 | 50 | 100 | 75 |
|  | 2 | 40 | 60 | 50 |
|  | 1 | 50 | 50 | 50 |
| cyano-(3-phenoxyphenyl)-methyl 4-chloro-α-(1-methylethyl)-benzene acetate | 1.6 | — | 100 | 100 |
|  | .8 | 80 | 50 | 65 |
|  | .4 | 70 | 70 | 70 |
|  | .2 | 70 | 30 | 50 |
|  | .1 | 60 | 0 | 30 |
| (3-phenoxybenzyl)-cis-trans-3-(2,2-dichlorovinyl)-2,2-dimethylcyclopropane carboxylate | 1.6 | — | 50 | 50 |
|  | .8 | 80 | 70 | 75 |
|  | .4 | 50 | 40 | 45 |
|  | .2 | 50 | 40 | 45 |
|  | .1 | 10 | 10 | 10 |
| N,N'-[thiobis(methylamino)-carbonyloxy]bis-[ethanimidothioic acid], dimethyl ester and cyano-(3-phenoxyphenyl)-methyl 4-chloro-α-(1-methylethyl)-benzene acetate | 4 +.4 | — | 70 | 70 |
|  | 4 +.2 | 60 | 100 | 80 |
|  | 4 +.1 | 90 | 80 | 85 |
|  | 2 +.2 | 90 | 100 | 95 |
|  | 2 +.1 | 50 | 50 | 50 |
| N,N'-[thiobis(methylamino-carbonyloxy)]-bis-[ethanimidothioic acids], dimethyl ester and (3-phenoxybenzyl)-cis-trans-3-(2,2-dichlorovinyl)-2,2-dimethylcyclopropane carboxylate. | 4 +.4 | — | 100 | 100 |
|  | 4 +.2 | 100 | 80 | 90 |
|  | 4 +.1 | 100 | 100 | 100 |
|  | 2 +.2 | 40 | 80 | 60 |
|  | 2 +.1 | 90 | 70 | 80 |

TEST 2

Insecticidal activity of the compounds and mixtures listed below at the stated concentration were determined on beet armyworm. Larvae (~35 mg in weight) maintained on modified Shorey's artificial diet were treated topically by microapplication of solutions of the individual compounds and mixtures. After treatment, they were replaced on modified Shorey's artificial diet until evaluations were made 2 days later. Results are recorded below.

| COMPOUND | μg/larvae | % mortality (48 hours) |  |
|---|---|---|---|
| N,N'-[thiobis(methyl-amino)carbonyloxy]bis-[ethanimidothioic acid], dimethyl ester | 6 | 93 | (Assigned ED$_{50}$ of 2 see Note 1) |
|  | 4 | 87 |  |
|  | 2 | 47 |  |
|  | 1 | 80 |  |
| cyano-(3-phenoxyphenyl)-methyl 4-chloro-α-(1-methylethyl)-benzene acetate | .02 | 80 | (Assigned ED$_{50}$ of 0.0015 see Note 1) |
|  | .01 | 20 |  |
|  | .005 | 40 |  |
| (3-phenoxybenzyl)-cis-trans-3-(2,2-dichlorovinyl)-2,2-dimethylcyclopropane carboxylate | .02 | 53 | (Assigned ED$_{50}$ of 0.02 see Note 1) |
|  | .01 | 27 |  |
|  | .005 | 0 |  |
| N,N'-[thiobis(methylamino)-carbonyloxy]bis-[ethanimidothioic acid], dimethyl ester and cyano-(3-phenoxyphenyl)-methyl 4-chloro-α-(1-methylethyl)-benzene acetate | 2 +.02 | 73 |  |
|  | 1 +.02 | 87 |  |
|  | 2 +.015 | 93 |  |
|  | 1 +.015 | 53 |  |
|  | 2 +.01 | 93 |  |
|  | 2 +.005 | 80 |  |
|  | 1 +.01 | 73 |  |
|  | 1 +.005 | 67 |  |
| N,N'-[thiobis(methylamino-carbonyloxy)]-bis-[ethanimidothioic acids], dimethyl ester and (3-phenoxybenzyl)-cis-trans-3-(2,2-dichlorovinyl)-2,2-dimethylcylopropane carboxylate. | 2 +.02 | 80 |  |
|  | 1 +.02 | 93 |  |
|  | 2 +.015 | 100 |  |
|  | 1 +.015 | 80 |  |
|  | 2 +.01 | 80 |  |
|  | 2 +.005 | 53 |  |
|  | 1 +.01 | 53 |  |
|  | 1 +.005 | 67 |  |

NOTE 1

For each of the three compounds tested individually, the data were analyzed and an ED$_{50}$ value, considered to be a fair and representative value from the data obtained, was assigned to aid in the comparative study of individual compounds vs combinations.

ANALYSIS OF TESTS 1 AND 2

For Test 1 and Test 2, the data was analyzed with the aid of a computer and FIG. 1, 2, 3 and 4 show plotted results. In each FIGURE, the solid line in the chart indicates the values which would be expected for each combination of compounds if the mortality results for each individual compound were additive, i.e., predicted results. The blocks or triangles indicate observed results, i.e., data from Test 1 and Test 2. Any value below the solid line indicates that the mortality results are less than additive for the combination of compounds. Any value above the solid line indicates that the mortality results are better than additive for combination of compounds in comparison to individual compounds.

The insecticidal use of a combination of N,N'-[thiobis(methylamino)carboxyloxy]bis[ethanimidothioic acid], dimethyl ester and either cyano-(3-phenoxyphenyl)methyl 4-chloro-α-(1-methylethyl)benzeneacetate or (3-phenoxybenzyl)cis-trans-3-(2,2-dichlorovinyl)-2,2-dimethylcyclopropanecarboxylate is superior to use of the three compounds individually since lower concentrations can be employed to obtain an equivalent insect mortality.

FORMULATION

Useful formulations containing the named insecticidally active ingredients can be prepared in conventional ways. They include dusts, granules, pellets, solutions, suspensions, emulsions, wettable powders, emulsifiable concentrates and the like. Many of these can be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredients and at least one of (a) about 0.1% to 20% surfactant(s) and (b) about 5% to 99% solid or liquid diluent(s). More specifically, they will generally contain these ingredients in the following proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredients can, of course, be present depending on the intended use and the physical properties of the compounds. Higher ratios of surfactant to active ingredients are sometimes desirable, and are achieved by incorporation into the formulation or by tank mixing.

Typical solid diluents are described in Watkins, et al., "Handbook of Insecticide Dust Diluents and Carriers," 2nd Edn., Dorland Books, Caldwell, N.J. The more absorptive diluents are preferred for wettable powders and the denser ones for dusts. Typical liquid diluents and solvents are described in Marsden, "Solvents Guide," 2nd Edn., Interscience, New York, 1950. Solubility under 0.1% is preferred for suspension concentrates; solution concentrates are preferably stable against phase separation at 0° C. "McCutcheon's Detergents and Emulsifiers Annual," Allured Publ. Corp., Ridgewood, N.J., as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer of fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," Chemical Engineering, Dec. 4, 1967, pp. 147ff, and "Perry's Chemical Engineer's Handbook," 4th Edn., McGraw-Hill, N.Y., 1963, pp. 8–59ff.

For further information regarding the art of formulation, see for example:

J. B. Buchanan, U.S. Pat. No. 3,576,834, Apr. 27, 1971, col. 5, line 36, through col. 7, line 70, and Examples 1–4, 17, 106, 123–140.

R. R. Shaffer, U.S. Pat. No. 3,560,616, Feb. 2, 1971, col. 3, line 48, through col. 7, line 26, Examples 3–9, 11–18.

E. Somers, "Formulation", Chapter 6 in Torgeson, "Fungicides", Vol. I, Academic Press, New York, 1967.

The following examples illustrate useful agricultural compositions which can be formulated.

EXAMPLE 3

AQUEOUS SUSPENSION

| | |
| --- | --- |
| N,N'-[thiobis(methylaminocarbonyloxy)]bis-[ethanimidothioic acid], dimethyl ester | 23.0% |
| (3-phenoxybenzyl)cis-trans-(2,2-dichlorovinyl)-2,2-dimethylcyclopropanecarboxylate | 2.0% |
| hydrated attapulgite | 3.0% |
| crude calcium ligninsulfonate | 10.0% |
| sodium dihydrogen phosphate | 0.5% |
| water | 61.5% |

The ingredients are ground together in a ball or roller mill until the solid particles have been reduced to diameters under 10 microns.

EXAMPLE 4

EMULSIFIABLE CONCENTRATE

| | |
| --- | --- |
| N,N'-[thiobis(methylamino)carbonyloxy]bis[ethanimidothioic acid], dimethyl ester | 27.0% |
| (3-phenoxybenzyl)cis-trans-3-(2,2-dichlorovinyl)-2,2-dimethylcyclopropanecarboxylate | 3.0% |
| blend of oil soluble sulfonates and polyoxyethylene ethers | 4.0% |
| xylene | 66.0% |

The ingredients are combined and stirred with gentle warming to speed solution. A fine screen filter is included in packaging operation to insure the absence of any extraneous undissolved material in the product.

EXAMPLE 5

EMULSIFIABLE CONCENTRATE

| | |
| --- | --- |
| N,N'-[thiobis(methylaminocarbonyloxy)]bis-[ethanimidothioic acid], dimethyl ester | 19.0% |
| (3-phenoxybenzyl)cis-trans-3-(2,2-dichlorovinyl)-2,2-dimethylcyclopropanecarboxylate | 1.0% |
| chlorobenzene | 74.0% |
| sorbitan monostearate and polyoxyethylene condensates thereof | 6.0% |

"Consisting essentially of" in the present disclosure is intended to have its customary meaning: namely, that all specified materials and conditions are very important in practicing the invention but that unspecified materials and conditions are not excluded so long as they do not prevent the benefits of the invention from being realized.

What is claimed is:

1. An insecticidal composition consisting essentially of
    (A) N,N'-[thiobis(methylaminocarbonyloxy]bis[ethanimidothioic acid], dimethyl ester; and
    (B) cyano-(3-phenoxyphenyl)-methyl 4-chloro-α-(1-methylethyl)benzeneacetate, or (3-phenoxybenzyl) cis-trans-3-(2,2-dichlorovinyl)-2,2-dimethylcyclopropanecarboxylate, wherein a ratio of (A) to (B) is in a range of from 20:1 to 3:1 by weight.

2. The insecticidal composition of claim 1 wherein said ratio is from 10:1 to 5:1 by weight.

3. The insecticidal composition of claim 1 where (A) is N,N'-[thiobis(methylaminocarbonyloxy]bis-[ethanimidothioic acid], dimethyl ester and (B) is cyano-(3-phenoxyphenyl)methyl 4-chloro-α-(1-methylethyl)-benzene acetate.

4. The insecticidal composition of claim 1 where (A) is N,N'-[thiobis(methylaminocarbonyloxy]bis-[ethanimidothioic acid], dimethyl ester and (B) is (3-phenoxybenzyl)cis-trans-3-(2,2-dichlorovinyl)-2,2-dimethylcyclopropanecarboxylate.

5. A method of control of insects comprising applying to a locus to be protected an insecticidally effective amount of the composition of claim 1.

6. A method of control of insects comprising applying to a locus to be protected an insecticidally effective amount of the composition of claim 2.

7. A method of control of insects comprising applying to a locus to be protected an insecticidally effective amount of the composition of claim 3.

8. A method of control of insects comprising applying to a locus to be protected an insecticidally effective amount of the composition of claim 4.

* * * * *